United States Patent

Swoboda

(12)

(10) Patent No.: US 6,169,116 B1
(45) Date of Patent: Jan. 2, 2001

(54) AMINO-TETRALINES, PHARMACEUTICAL COMPOSITIONS CONTAINING THEM AND THEIR PHARMACEUTICAL USES

(75) Inventor: Robert Swoboda, Koeniz (CH)

(73) Assignee: Novartis AG, Basel (CH)

( * ) Notice: Under 35 U.S.C. 154(b), the term of this patent shall be extended for 0 days.

(21) Appl. No.: 09/340,818

(22) Filed: Jun. 28, 1999

Related U.S. Application Data

(63) Continuation of application No. 08/945,721, filed as application No. PCT/EP96/01841 on May 3, 1996.

(30) Foreign Application Priority Data

May 5, 1995 (GB) .................................... 9509156

(51) Int. Cl.$^7$ ........................ A61K 31/136; C07C 211/60
(52) U.S. Cl. ...................... 514/657; 514/517; 514/524; 514/603; 514/619; 514/654; 514/655; 558/48; 558/418; 558/420; 564/86; 564/164; 564/167; 564/374; 564/391; 564/428
(58) Field of Search ................... 514/647, 524, 514/619, 657; 564/305, 164, 428; 558/418

(56) References Cited

U.S. PATENT DOCUMENTS

| | | | |
|---|---|---|---|
| 5,472,979 | 12/1995 | Lavielle et al. | 514/562 |
| 5,635,537 | 6/1997 | Andén et al. | 514/657 |
| 5,644,024 | 7/1997 | Abrecht et al. | 530/317 |

FOREIGN PATENT DOCUMENTS

| | | |
|---|---|---|
| 257285 A2 | 3/1988 | (EP) . |
| 270947 B1 | 6/1988 | (EP) . |
| 378456 B1 | 7/1990 | (EP) . |
| 381902 A1 | 8/1990 | (EP) . |
| 383318 B1 | 8/1990 | (EP) . |
| 399982 | 11/1990 | (EP) . |
| 640618 | 3/1995 | (EP) . |
| 648741 | 4/1995 | (EP) . |

OTHER PUBLICATIONS

Hiraoka, Masayuki, et al. Chemical Abstracts, vol. 91, No. 3, Jul. 16, 1979, Abstract No. 20185w, p. 625.
Liu, Ye. et al., Eur. J. Med. Chem, 30(4) pp. 277–286 (1995).
Liu, Ye et al., J. Med. Chem., 36 (26) pp. 4221–4229 (1993).
Cozzi, Paolo et al., J. Med. Chem., 29(3), pp. 404–410, (1986).
Itoh, Katsumi et al., Chem. Pharm Bull., 32(1), pp. 130–151 (1984).
Liu, Ye et. al., Chemical Abstract, vol. 115, No. 15, Oct. 14, 1991, Abs. # 158677d., p. 891.

*Primary Examiner*—Richard L. Raymond
(74) *Attorney, Agent, or Firm*—Joseph J. Borovian

(57) ABSTRACT

Compounds of formula I

I

[chemical structure of a tetraline with R$_1$, R$_2$ on phenyl ring, R$_3$ substituent, and N(R$_4$)(R$_5$) group]

wherein R$_1$, R$_2$, R$_3$, R$_4$ and R$_5$ are as defined in the description, are useful as pharmaceuticals.

7 Claims, No Drawings

AMINO-TETRALINES, PHARMACEUTICAL COMPOSITIONS CONTAINING THEM AND THEIR PHARMACEUTICAL USES

This is a continuation of U.S. application Ser. No. 08/945,721, having a 371 date of Nov. 5, 1997, which application is a 371 of International Application No. PCT/EP96/01841, now abandoned, filed May 3, 1996.

The present invention relates to novel amino-tetralines (tetrahydro-naphthalenamines), their preparation, their use as pharmaceuticals and pharmaceutical compositions containing them.

In accordance with the invention, there are provided, in a first aspect, 1,2,3,4-tetrahydro-2-naphthalenamines bearing a phenyl substituent on the aromatic ring and acid addition salt thereof.

The phenyl substituent is preferably in position 5 of the 2-naphthalenamine.

The phenyl substituent may bear further substituents, for example as in the case of formula I below.

Further substituents may also be present conveniently but not exclusively on the aromatic ring, e.g. in position 8 of the 2-naphthalenamine when the phenyl group is in position 5.

More particularly the present invention provides a compound of formula I

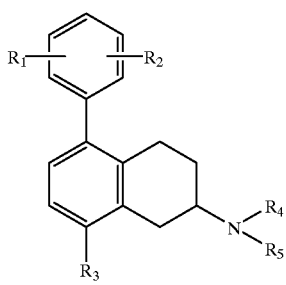

I wherein $R_1$ and $R_2$, independently, are hydrogen, $(C_{1-4})$alkyl, $(C_{1-4})$alkoxy, $(C_{1-4})$alkylthio, halogen, trifluoromethyl, trifluoromethoxy, cyano, $(C_{2-5})$alkanoyl, $(C_{1-4})$alkylsulfonyl or sulfamoyl, $R_3$ is hydrogen, hydroxy, $(C_{1-4})$alkyl, $(C_{1-4})$alkoxy, halogen, cyano, $(C_{2-5})$alkanoyl, carbamoyl, $(C_{1-4})$alkylsulfonyloxy or trifluoromethylsulfonyloxy, and $R_4$ and $R_5$, independently, are hydrogen, $(C_{1-4})$alkyl, hydroxy$(C_{2-4})$alkyl or phenyl$(C_{1-4})$alkyl, or form together with the nitrogen atom to which they are attached a pyrrolidinyl, piperidino or piperazinyl group,
in free base or acid addition salt form.

Halogen is fluorine, chlorine, bromine or iodine, preferably fluorine or chlorine.

Any alkyl, alkoxy and alkylthio radicals preferably are straight chain radicals. They preferably have 1 to 3 carbon atoms, more preferably they are methyl, methoxy and methylthio groups.

The following significances and their combinations are preferred:

$R_1$ and $R_2$, independently, are hydrogen, $(C_{1-4})$alkyl, $(C_{1-4})$alkoxy, halogen or trifluoromethyl, $R_3$ is hydrogen, hydroxy, $(C_{1-4})$alkoxy, cyano or carbamoyl, $R_4$ and $R_5$, independently, are hydrogen or $(C_{1-4})$alkyl, or form together with the nitrogen to which they are attached a piperidino group.

In a particular group of compounds of formula I, $R_1$ and $R_2$, independently, are hydrogen, $(C_{1-4})$alkyl, $(C_{1-4})$alkoxy, $(C_{1-4})$alkylthio, halogen, trifluoromethyl, cyano or $(C_{2-5})$alkanoyl, $R_3$ is as defined on line 5 and 6 and $R_4$ and $R_5$, independently, are hydrogen, $(C_{1-4})$alkyl or phenyl$(C_{1-4})$alkyl, or form together with the nitrogen atom to which they are attached a pyrrolidinyl, piperidino or piperazinyl group.

The compounds of the invention possess an asymmetrical carbon atom in position 2. They may therefore appear in optically active form or in form of mixtures of optical isomers, e.g. in form of racemic mixtures. All optical isomers and their mixtures including the racemic mixtures are part of the present invention.

When a compound of the invention is in optically active form, the R configuration is preferred.

In a further aspect, the invention provides a process for the production of the compounds of the invention, whereby a 1,2,3,4-tetrahydro-2-naphthalenamine bearing a halogen on the aromatic ring is reacted with optionally substituted phenylboronic acid and the resulting compound is recovered in free base form or in acid addition salt form.

More particularly the invention provides a process for the production of the compounds of the invention, whereby a compound of formula II

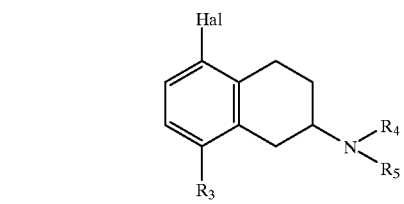

II wherein $R_3$, $R_4$ and $R_5$ are as defined above and Hal is halogen, is reacted with a compound of formula III

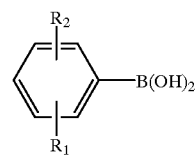

III wherein $R_1$ and $R_2$ are as defined above, and the resulting compound is recovered in free base form or in acid addition salt form.

The reaction may be effected in known manner, preferably by transition metal-catalyzed aryl-aryl coupling, e.g. as described in Example 1. Hal is preferably bromine or iodine, particularly bromine.

Working up of the reaction mixtures obtained according to the above process and purification of the compounds thus obtained may be carried out in accordance to known procedures.

Acid addition salts may be produced in known manner from the free base forms and vice-versa. Suitable pharmaceutically acceptable acid addition salts for use in accordance with the present invention include for example the hydrochloride, the hydrogen maleate, the hydrogen fumarate and the hydrogen malonate.

Racemic compounds of the invention may be obtained from racemic starting materials. Optically active isomers may be obtained form optically active starting materials or from the racemate. The enantiomers may be obtained from the racemate by known methods, for example by fractional crystallization of diastereoisomeric salts, e.g. their salts with (+)-di-O,O'-p-toluoyl-D-tartaric acid or (−)-di-O,O'-p-toluoyl-L-tartaric acid.

The starting materials of formula II may be produced by halogenating compounds of formula IV

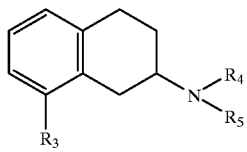

wherein $R_3$, $R_4$ and $R_5$ are as defined above, in accordance to known procedures, e.g. as described in Example 1.

The starting materials of formulae III and IV are known or may be produced in analogous manner to known procedures.

Compounds of the invention, e.g. compounds of formula I and their pharmaceutically acceptable acid addition salts, hereinafter referred to as agents of the invention, exhibit pharmacological activity and are, therefore, useful as pharmaceuticals.

The agents of the invention provide long-lasting protection against maximal electroshock-induced convulsions in mice at doses of about 1 to 100 mg/kg p.o. and about 0.32 to 32 mg/kg i.p. [cf. E. A. Swinyard, J. Am. Pharm. Assoc. Scient. Ed. 38, 201 (1949) and J. Pharmacol. Exptl. Therap. 106, 319 (1952)].

The agents of the invention are therefore useful in the treatment of epilepsy and other convulsive states such as high pressure neurological syndrome.

Furthermore, the agents of the invention reduce ischemia-induced neuronal damage and ensuing symptoms in the middle cerebral artery (MCA) occlusion model in rats at a dosage of 1–30 mg/kg i.p, i.v. and p.o. [cf. A. Tamura et al., J. Cereb. Blood Flow Metabol. 1, 53–60 (1981)), A. Sauter, M. Rudin, Stroke 17, 1228–1234 (1986)].

The agents of the invention are therefore useful in the treatment of any clinical condition involving a component of cerebral anoxia, hypoxia and/or ischemia, e.g. ischemic damage to grey and white matter, stroke, subarachnoid hemorrhage, brain and spinal cord injury/trauma, high intracranial pressure, mult-infarct dementia or vascular dementia, and any surgical procedure potentially associated with cerebral anoxia, hypoxia and/or ischemia (e.g. cardiac bypass, operations on extracerebral vessels).

The agents of the invention display binding to the veratridine-sensitive sodium channel with $IC_{50}S$ of from about 0.1 to about 100 $\mu M$. For the binding procedure see for example J. B. Brown, Journal of Neuroscience 6, 2064–2070 (1986). They block veratridine-induced glutamate release in rat hippocampal slice preparations at concentrations of about 0.1–1 $\mu M$.

The experiment is performed according to a modification of M. J. Leach et al. in Epilepsia 27, 490–497 (1986) and Stroke 24, 1063–1067 (1993), using exogenous glutamate.

As a result, the agents of the invention are indicated for the treatment of any pathology, disorder or clinical condition involving glutamate release in their etiology, including psychiatric disorders (such as schizophrenia, depression, anxiety, panic attacks, attention deficit and cognitive disorders, social withdrawal), hormonal conditions (excess GH [e.g. in the treatment of diabetes mellitus, angiopathy and acromegaly] or LH [prostate hypertrophy, menopausal syndrome] secretion, corticosterone secretion in stress), metabolic induced brain damage (hypolycemia, non-ketotic hyperglycinaemia [glycine encephalopathy], sulphite oxidase deficiency, hepatic encephalopathy associated with liver failure), emesis, spasticity, tinnitus, pain (e.g. cancer pain, arthritis) and drug (ethanol, opiates [including synthetics with opiate-like effects, e.g. pethidine, methadone etc.], cocaine, amphetamine, barbiturates and other sedatives, benzodiazepines) abuse and withdrawal.

Moreover, the agents of the invention are indicated in the treatment of any pathology involving neuronal damage, for example neurodegenerative disorders such as Alzheimer's, Huntington's or Parkinson's diseases, virus (including HIV)-induced neurodegeneration, Amyotrophic lateral sclerosis (ALS), supra-nuclear palsy, olivoponto-cerebellar atrophy (OPCA), and the actions of environmental, exogenous neurotoxins.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 0.5 to about 100 mg/kg animal body weight. In larger mammals, for example humans, an indicated daily dosage is in the range from about 1 to about 500, preferably from about 1 to about 300 mg of an agent of the invention, conveniently administered, for example, in divided doses up to four times a day or in sustained release form.

For all these indications the preferred compound is (R)-1,2,3,4-tetrahydro-8-methoxy-N,N-dimethyl-5-[4-(trifluoromethyl)phenyl]-2-naphthaleneamine, which is the compound of example 21. It has for example been determined that in the above mentioned electroshock model, this compound provides protection against maximal electroshock-induced convulsions with a threshold dose of 10 mg/kg p.o. for periods up to 8 hours post-administration. In the MCA occlusion model, the compound given i.p. immediately after occlusion has been found to dose-dependently reduce infarct size at 3.2, 10 and 32 mg/kg (19, 43, and 53% respectively). In the veratridine-induced glutamate release test, the compound has been found to block the release with an $IC_{50}$ of 0.5 $\mu M$, which is consistent with its affinity for the veratridine binding site ($IC_{50}$=125 nM).

The compound of example 21 is for example superior to the standard Lifarizine in the MCA occlusion model (infarct size reduction of 43% versus 25%, after 10 mg/kg i.p.). In the veratridine-induced glutamate release test it has been found to be about equipotent to Lifarizine, but more potent than the standards Riluzole and Lamotrigine ($IC_{50}$=0.5 $\mu M$ versus 5 $\mu M$ and 20 $\mu M$ respectively).

The preferred indications are epilepsy, stroke and brain and spinal trauma.

The agents of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of epilepsy, stroke and brain or spinal trauma.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from 0.25 to about 25 mg of a compound according to the invention.

Moreover the present invention provides the use of an agent of the invention, for the manufacture of a medicament for the treatment of any condition mentioned above, e.g. epilepsy, stroke and brain or spinal trauma.

In still a further aspect, the present invention provides a method for the treatment of any condition mentioned above, e.g. epilepsy, stroke and brain or spinal trauma, in a subject in need of such treatment, which comprises administering to such subject a therapeutically effective amount of an agent of the invention.

The following examples illustrate the invention. The temperatures are given in degrees Celsius and are uncorrected.

EXAMPLE 1

(+/−)-1,2,3,4-tetrahydro-5-(4-chlorophenyl)-8-methoxy-N,N-dimethyl-2-naphthalenamine 0.57 g (2 mMol) of (+/−)-1,2,3,4-tetrahydro-5-bromo-8-methoxy-N,N-dimethyl-2-naphthalenamine are dissolved in 8 ml toluene. 0.55 g (3.54 mMol) of 4-chlorophenylboronic acid, 0.07 g (0.23 mMol) of tri(ortho-tolyl)phosphine, 3 ml of 2N aqueous sodium carbonate and 0.7 ml of methanol are added. After degassing and filling the system with argon, 0.031 g (0.14 mMol) of palladium(II)acetate are added and the mixture is stirred overnight at 80°. The aqueous phase is separated and extracted with ethylacetate. The combined organic phases are extracted with 2N acetic acid, the acidic extracts basified with aqueous ammonia and again extracted with ethylacetate. After drying with sodium sulfate, filtering and evaporating the organic phase, the resulting bright-brown oil is treated with fumaric acid in methyl-tert.butylether. The resulting salt is recrystallised from isopropanol, yielding white crystals of the hydrogen fumarate of the title compound, m.p. 213–216°.

The starting material may be produced as follows:

4.1 g (20 mMol) of (+/−)-1,2,3,4-tetrahydro-8-methoxy-N,N-dimethyl-2-naphthalenamine are dissolved in 50 ml of acetic acid and 1.8 (22 mMol) of sodium acetate are added. A solution of 1.02 ml (20 mMol) of bromine in 5 ml acetic acid is added dropwise at room temperature within about 30 minutes. A colorless precipitate is formed. After stirring overnight solvent is distilled off under vacuum, the residue taken up with water and extracted with ethylacetate. The remaining aqueous phase is made alkaline with aqueous ammonia and extracted with ethylacetate. The organic phase is dried with sodium sulfate, filtered and evaporated to dryness. The remaining oil is distilled in a bulb to bulb distillation apparatus yielding a slightly yellow oil, b.p. 170–180° at 0.04 mbar.

The following compounds are prepared analogously to example 1.

| Ex. | $R_1$ | $R_2$ | $R_3$ | $R_4$ | $R_5$ | Config. * | M.p. (salt) |
|---|---|---|---|---|---|---|---|
| 2  | H      | H     | OMe   | Me       | Me       | +/−     | 171–174° (1) |
| 3  | 2-Cl   | "     | "     | "        | "        | "       | 186–190° (1) |
| 4  | 2-Me   | "     | "     | "        | "        | "       | 190–196° (1) |
| 5  | 2-OMe  | "     | "     | "        | "        | "       | 252–263° (2) |
| 6  | H      | "     | OH    | "        | "        | "       | 223–229° (3) |
| 7  | "      | "     | H     | "        | "        | "       | 130–133° (1) |
| 8  | 4-Me   | "     | OMe   | "        | "        | "       | 205–209° (4) |
| 9  | 4-$CF_3$ | "   | "     | "        | "        | "       | 202–207° (4) |
| 10 | 2-Cl   | 4-Cl  | "     | "        | "        | "       | 250–257° (2) |
| 11 | 2-F    | H     | "     | "        | "        | "       | 200–209° (4) |
| 12 | 3-Cl   | "     | "     | "        | "        | "       | 187–190° (1) |
| 13 | 2-Cl   | "     | "     | "        | "        | (−)-(S) | 200–225° (4) |
| 14 | "      | "     | "     | "        | H        | "       | 219–224° (4) |
| 15 | "      | "     | "     | "        | Me       | (+)-(R) | 221–226° (4) |
| 16 | "      | "     | "     | "        | H        | "       | 216–223° (4) |
| 17 | H      | "     | "     | piperidino |        | +/−     | 239–245° (4) |
| 18 | 2-Cl   | "     | "     | "        |          | "       | 204–210° (4) |
| 19 | H      | "     | "     | n-Propyl | n-Propyl | "       | 130–145° (1) |
| 20 | 4-$CF_3$ | "   | "     | Me       | Me       | (−)-(S) | 212–215° (4) |
| 21 | "      | "     | "     | "        | "        | (+)-(R) | 209–216° (4) |
|    |        |       |       |          |          |         | 75–82° (3) |
| 22 | "      | "     | OH    | "        | "        | "       | 224–263° (2)* |
| 23 | 2-Et   | "     | OMe   | "        | "        | +/−     | 189–197° (4) |
| 24 | 2-Cl   | "     | CN    | "        | "        | "       | 209–215° (4) |
| 25 | "      | 4-F   | OMe   | "        | "        | "       | 236–240° (2) |
| 26 | 2-F    | "     | "     | "        | "        | "       | 172–178° (1) |
| 27 | 2-OMe  | 4-OMe | "     | "        | "        | "       | 182–189° (4) |
| 28 | 2-F    | 3-F   | "     | "        | "        | "       | 193–211° (4) |
| 29 | 2-OMe  | 3-OMe | "     | "        | "        | "       | 213–229° (4) |
| 30 | 2-Me   | 5-Me  | "     | "        | "        | "       | 212–220° (4) |
| 31 | 2-Cl   | 3-Cl  | "     | "        | "        | "       | 198–208° (4) |
| 32 | 2-F    | 5-F   | "     | "        | "        | "       | 189–195° (1) |
| 33 | 2-Me   | 4-Me  | "     | "        | "        | "       | 232–238° (2) |
| 34 | 2-Cl   | H     | $CONH_2$ | "    | "        | "       | 186–189° (3) |
| 35 | 4-$CF_3$ | "   | OMe   | "        | H        | (+)-R   | 205–208° (4) |
| 36 | H      | "     | "     | "        | Me       | "       | 198–211° (4) |
| 37 | 4-Me   | "     | "     | "        | "        | "       | 194–202° (4) |
| 38 | 4-Cl   | "     | "     | "        | "        | "       | 196–203° (4) |
| 39 | 4-OMe  | "     | "     | "        | "        | "       | 235–239° (4) |

-continued

| Ex. | $R_1$ | $R_2$ | $R_3$ | $R_4$ | $R_5$ | Config.* | M.p. (salt) |
|---|---|---|---|---|---|---|---|
| 40 | 4-F | " | " | " | " | " | 199–212° (1) |
| 41 | 4-CF$_3$ | " | " | (CH$_2$)$_2$—OH | " | " | 185–112° (4) |
| 42 | " | " | H | Me | " | " | 140–143° (5) |

Me = methyl
Et = ethyl
*decomposition
(1) hydrogen maleate
(2) hydrochloride
(3) free base
(4) hydrogen fumarate
(5) hydrogen malonate

What is claimed is:

1. A compound of formula I

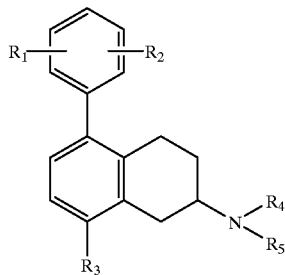

wherein
- $R_1$ and $R_2$, independently, are hydrogen, $(C_{1-4})$alkyl, $(C_{1-4})$alkoxy, $(C_{1-4})$alkylthio, halogen, trifluoromethyl, trifluoromethoxy, cyano, $(C_{2-5})$alkanoyl, $(C_{1-4})$alkylsulfonyl or sulfamoyl,
- $R_3$ is hydrogen, hydroxy, $(C_{1-4})$alkyl, $(C_{1-4})$alkoxy, halogen, cyano, $(C_{2-5})$alkanoyl, carbamoyl, $(C_{1-4})$alkylsulfonyloxy or trifluoromethylsulfonyloxy, and
- $R_4$ and $R_5$, independently, are hydrogen, $(C_{1-4})$alkyl, hydroxy$(C_{2-4})$alkyl or phenyl$(C_{1-4})$alkyl, in free base or acid addition salt form.

2. A compound of claim 1 wherein
- $R_1$ and $R_2$, independently, are hydrogen, $(C_{1-4})$alkyl, $(C_{1-4})$alkoxy, halogen, trifluoromethyl, cyano, $(C_{2-5})$alkanoyl or $(C_{1-4})$alkylthio,
- $R_3$ is hydrogen, hydroxy, $(C_{1-4})$alkyl, $(C_{1-4})$alkoxy, halogen, cyano, $(C_{2-5})$alkanoyl, carbamoyl, $(C_{1-4})$alkylsulfonyloxy or trifluoromethylsulfonyloxy, and
- $R_4$ and $R_5$, independently, are hydrogen, $(C_{1-4})$alkyl or phenyl$(C_{1-4})$alkyl, in free base or acid addition salt form.

3. A compound of claim 1 selected from the compounds of formula I, in optically active or racemic form, wherein:

| | | | | |
|---|---|---|---|---|
| $R_1$ = 4-Cl, | $R_2$ = H, | $R_3$ = OMe, | $R_4$ = Me, | $R_5$ = Me, |
| $R_1$ = H, | $R_2$ = H, | $R_3$ = OMe, | $R_4$ = Me, | $R_5$ = Me, |
| $R_1$ = 2-Cl, | $R_2$ = H, | $R_3$ = OMe, | $R_4$ = Me, | $R_5$ = Me, |
| $R_1$ = 2-Me, | $R_2$ = H, | $R_3$ = OMe, | $R_4$ = Me, | $R_5$ = Me, |
| $R_1$ = 2-OMe, | $R_2$ = H, | $R_3$ = OMe, | $R_4$ = Me, | $R_5$ = Me, |
| $R_1$ = H, | $R_2$ = H, | $R_3$ = OH, | $R_4$ = Me, | $R_5$ = Me, |
| $R_1$ = H, | $R_2$ = H, | $R_3$ = H, | $R_4$ = Me, | $R_5$ = Me, |
| $R_1$ = 4-Me, | $R_2$ = H, | $R_3$ = OMe, | $R_4$ = Me, | $R_5$ = Me, |
| $R_1$ = 4-CF$_3$, | $R_2$ = H, | $R_3$ = OMe, | $R_4$ = Me, | $R_5$ = Me, |
| $R_1$ = 2-Cl, | $R_2$ = 4-Cl, | $R_3$ = OMe, | $R_4$ = Me, | $R_5$ = Me, |
| $R_1$ = 2-F, | $R_2$ = H, | $R_3$ = OMe, | $R_4$ = Me, | $R_5$ = Me, |
| $R_1$ = 3-Cl, | $R_2$ = H, | $R_3$ = OMe, | $R_4$ = Me, | $R_5$ = Me, |
| $R_1$ = 2-Cl, | $R_2$ = H, | $R_3$ = OMe, | $R_4$ + $R_5$ = piperidino, | |
| $R_1$ = H, | $R_2$ = H, | $R_3$ = OMe, | $R_4$ = n-Pr, | $R_5$ = n-Pr, |
| $R_1$ = 4-CF$_3$, | $R_2$ = H, | $R_3$ = OH, | $R_4$ = Me, | $R_5$ = Me, |
| $R_1$ = 2-Et, | $R_2$ = H, | $R_3$ = OMe, | $R_4$ = Me, | $R_5$ = Me, |
| $R_1$ = 2-Cl, | $R_2$ = H, | $R_3$ = CN, | $R_4$ = Me, | $R_5$ = Me, |
| $R_1$ = 2-Cl, | $R_2$ = 4-F, | $R_3$ = OMe, | $R_4$ = Me, | $R_5$ = Me, |
| $R_1$ = 2-F, | $R_2$ = 4-F, | $R_3$ = OMe, | $R_4$ = Me, | $R_5$ = Me, |
| $R_1$ = 2-OMe, | $R_2$ = 4-OMe, | $R_3$ = OMe, | $R_4$ = Me, | $R_5$ = Me, |
| $R_1$ = 2-F, | $R_2$ = 3-F, | $R_3$ = OMe, | $R_4$ = Me, | $R_5$ = Me, |
| $R_1$ = 2-OMe, | $R_2$ = 3-OMe, | $R_3$ = OMe, | $R_4$ = Me, | $R_5$ = Me, |
| $R_1$ = 2-Me, | $R_2$ = 5-Me, | $R_3$ = OMe, | $R_4$ = Me, | $R_5$ = Me, |
| $R_1$ = 2-Cl, | $R_2$ = 3-Cl, | $R_3$ = OMe, | $R_4$ = Me, | $R_5$ = Me, |
| $R_1$ = 2-F, | $R_2$ = 5-F, | $R_3$ = OMe, | $R_4$ = Me, | $R_5$ = Me, |
| $R_1$ = 2-Me, | $R_2$ = 4-Me, | $R_3$ = OMe, | $R_4$ = Me, | $R_5$ = Me, |
| $R_1$ = 2-Cl, | $R_2$ = H, | $R_3$ = CONH$_2$, | $R_4$ = Me, | $R_5$ = Me, |
| $R_1$ = 4-CF$_3$, | $R_2$ = H, | $R_3$ = OMe, | $R_4$ = Me, | $R_5$ = H, |
| $R_1$ = 4-OMe, | $R_2$ = H, | $R_3$ = OMe, | $R_4$ = Me, | $R_5$ = Me, |
| $R_1$ = 4-F, | $R_2$ = H, | $R_3$ = OMe, | $R_4$ = Me, | $R_5$ = Me, |
| $R_1$ = 4-CF$_3$, | $R_2$ = H, | $R_3$ = OMe, | $R_4$ = Et—OH, | $R_5$ = Me, and |
| $R_1$ = 4-CF$_3$, | $R_2$ = H, | $R_3$ = H, | $R_4$ = Me, | $R_5$ = Me |

Me being methyl, Et ethyl and Pr propyl, in free base or acid addition salt form.

4. A compound of claim 1 which is (R)-1,2,3,4-tetrahydro-8-methoxy-N,N-dimethyl-5-[4-(trifluoromethyl)phenyl]-2-naphthalenamine, in free base or acid addition salt form.

5. A process for production of a compound of formula I as defined in claim 1, in free base or acid addition salt form, whereby a compound of formula II,

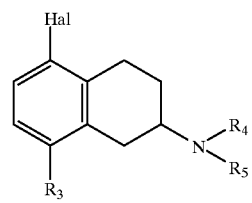

wherein $R_3$, $R_4$ and $R_5$ are as defined in claim 2 and Hal is halogen, is reacted with a compound of formula III

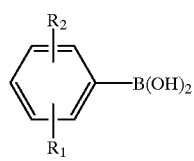

wherein $R_1$ and $R_2$ are as defined in claim 2, and the resulting compound is recovered in free base form or in acid addition said form.

6. A pharmaceutical composition comprising a pharmaceutically acceptable carrier or diluent and a therapeutically effective amount of a compound according to claim 1, in free base or pharmaceutically acceptable acid addition salt form.

7. A method for treating epilepsy, stroke, brain trauma or spinal trauma comprising administering to a subject in need of such treatment a therapeutically effective amount of a compound according to claim 1, in free base or pharmaceutically acceptable acid addition salt form.

* * * * *

UNITED STATES PATENT AND TRADEMARK OFFICE
CERTIFICATE OF CORRECTION

PATENT NO. : 6,169,116 B1
DATED : January 2, 2001
INVENTOR(S) : Robert Swoboda

It is certified that error appears in the above-identified patent and that said Letters Patent is hereby corrected as shown below:

Column 1,
Line 16, change "salt" to -- salts --.

Column 2,
Line 4, should read: -- alkanoyl, $R_3$ is as defined above on lines 5 and 6 and $R_4$ and $R_5$, --.
Line 66, change "form" to -- from --.

Column 3,
Line 46, change "mult-infarct" to -- multi-infarct --.

Column 4,
Line 2, change "hypolycemia" to -- hypoglycemia --.
Line 3, change "hyperglycinaemia" to -- hyperglycinemia --.

Column 6,
Line 15, after the number "1.8", insert -- g --.
Line 19, after "overnight", insert -- the --.

Column 8, claim 3,
In the continuation of the table, change "$R_4+R_5$=piperdino" to -- $R_4$=Me, $R_5$=H --.

Column 8, claim 5,
Line 1, after "for", insert -- the --.
Line 1, beneath the structural formula, after "claim", change "2" to -- 1 --.

UNITED STATES PATENT AND TRADEMARK OFFICE
CERTIFICATE OF CORRECTION

PATENT NO.   : 6,169,116 B1
DATED        : January 2, 2001
INVENTOR(S)  : Robert Swoboda It is certified that error appears in the above-identified patent and that said Letters Patent is hereby corrected as shown below:

Column 9, claim 5,
Line 1, beneath the structural formula, after "claim", change "2" to -- 1 --.

Column 9,
Last line, change "said" to -- salt --.

Signed and Sealed this

Twenty-ninth Day of January, 2002

Attest:

JAMES E. ROGAN
Attesting Officer         Director of the United States Patent and Trademark Office